(12) United States Patent
Mujkanovic

(10) Patent No.: US 8,052,717 B2
(45) Date of Patent: Nov. 8, 2011

(54) EMBOLIC PROTECTION DEVICE

(75) Inventor: Husnija Mujkanovic, Santa Clara, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 553 days.

(21) Appl. No.: 12/172,593

(22) Filed: Jul. 14, 2008

(65) Prior Publication Data

US 2010/0010534 A1    Jan. 14, 2010

(51) Int. Cl.
*A61M 29/00* (2006.01)
(52) U.S. Cl. ...................................................... 606/200
(58) Field of Classification Search .................. 606/200
See application file for complete search history.

(56) References Cited

U.S. PATENT DOCUMENTS

| | | | |
|---|---|---|---|
| 5,814,064 A * | 9/1998 | Daniel et al. ................. | 606/200 |
| 5,833,671 A * | 11/1998 | Macoviak et al. ........... | 604/247 |
| 5,954,745 A * | 9/1999 | Gertler et al. ................ | 606/200 |
| 6,086,605 A * | 7/2000 | Barbut et al. ................. | 606/200 |
| 6,142,987 A * | 11/2000 | Tsugita ......................... | 604/500 |
| 6,245,087 B1 * | 6/2001 | Addis ........................... | 606/200 |
| 6,494,895 B2 * | 12/2002 | Addis ........................... | 606/200 |
| 6,540,768 B1 * | 4/2003 | Diaz et al. .................... | 606/200 |
| 6,575,996 B1 * | 6/2003 | Denison et al. .............. | 606/200 |
| 6,663,650 B2 * | 12/2003 | Sepetka et al. ............... | 606/200 |
| 6,918,921 B2 * | 7/2005 | Brady et al. .................. | 606/200 |
| 6,969,396 B2 * | 11/2005 | Krolik et al. ................. | 606/200 |
| 6,974,469 B2 * | 12/2005 | Broome et al. ............... | 606/200 |
| 7,083,633 B2 * | 8/2006 | Morrill et al. ................ | 606/200 |
| 7,137,991 B2 * | 11/2006 | Fedie ............................ | 606/200 |
| 7,174,636 B2 * | 2/2007 | Lowe ........................... | 29/896.62 |
| 7,252,675 B2 * | 8/2007 | Denison et al. .............. | 606/200 |
| 7,285,126 B2 * | 10/2007 | Sepetka et al. ............... | 606/200 |
| 7,344,549 B2 * | 3/2008 | Boyle et al. .................. | 606/200 |
| 7,510,565 B2 * | 3/2009 | Gilson et al. ................. | 606/200 |
| 7,537,600 B2 * | 5/2009 | Eskuri .......................... | 606/200 |
| 7,537,601 B2 * | 5/2009 | Cano et al. ................... | 606/200 |
| 7,578,830 B2 * | 8/2009 | Kusleika et al. ............. | 606/194 |
| 7,651,514 B2 * | 1/2010 | Salahieh et al. ............. | 606/200 |
| 7,727,243 B2 * | 6/2010 | Sepetka et al. ............... | 606/127 |
| 2001/0044632 A1 * | 11/2001 | Daniel et al. ................. | 606/200 |
| 2002/0002383 A1 * | 1/2002 | Sepetka et al. ............... | 606/200 |
| 2002/0022858 A1 * | 2/2002 | Demond et al. .............. | 606/200 |
| 2002/0165576 A1 * | 11/2002 | Boyle et al. .................. | 606/200 |
| 2003/0130684 A1 * | 7/2003 | Brady et al. .................. | 606/200 |
| 2003/0176884 A1 * | 9/2003 | Berrada et al. ............... | 606/200 |
| 2003/0187474 A1 * | 10/2003 | Keegan et al. ............... | 606/200 |
| 2004/0073253 A1 * | 4/2004 | Morrill et al. ................ | 606/200 |
| 2004/0093012 A1 * | 5/2004 | Cully et al. ................... | 606/200 |
| 2004/0153119 A1 * | 8/2004 | Kusleika et al. ............. | 606/200 |
| 2004/0254601 A1 * | 12/2004 | Eskuri .......................... | 606/200 |
| 2005/0283186 A1 * | 12/2005 | Berrada et al. ............... | 606/200 |
| 2006/0190025 A1 * | 8/2006 | Lehe et al. .................... | 606/200 |
| 2006/0229658 A1 * | 10/2006 | Stivland ....................... | 606/200 |
| 2007/0233183 A1 | 10/2007 | Brady et al. | |
| 2007/0270900 A1 * | 11/2007 | Renati et al. ................. | 606/200 |

FOREIGN PATENT DOCUMENTS

| | | |
|---|---|---|
| WO | 03/073961 A1 | 9/2003 |
| WO | 2006108186 A1 | 10/2006 |

* cited by examiner

*Primary Examiner* — Gary Jackson
*Assistant Examiner* — Erin Colello
(74) *Attorney, Agent, or Firm* — Seager, Tufte & Wickhem, LLC

(57) ABSTRACT

The invention provides an embolic filter, a support structure therefor, and methods for preparing said filter for retrieval.

11 Claims, 14 Drawing Sheets

EMBOLIC PROTECTION DEVICE

TECHNICAL FIELD

This disclosure relates generally to embolic filters, support structures therefor, and methods for preparing said filters for retrieval.

BACKGROUND

Human blood vessels often become occluded or blocked by plaque, thrombi, other deposits, or material that reduce the blood carrying capacity of the vessel. Should the blockage occur at a critical place in the circulatory system, serious and permanent injury, and even death, can occur. To prevent this, some form of medical intervention is usually performed when significant occlusion is detected.

Several procedures are now used to open these stenosed or occluded blood vessels in a patient caused by the deposit of plaque or other material on the walls of the blood vessels. Angioplasty, for example, is a widely known procedure wherein an inflatable balloon is introduced into the occluded region. The balloon is inflated, dilating the occlusion, and thereby increasing the intraluminal diameter.

Another procedure is atherectomy. During atherectomy, a catheter is inserted into a narrowed artery to remove the matter occluding or narrowing the artery, i.e., fatty material. The catheter includes a rotating blade or cutter disposed in the tip thereof. Also located at the tip are an aperture and a balloon disposed on the opposite side of the catheter tip from the aperture. As the tip is placed in close proximity to the fatty material, the balloon is inflated to force the aperture into contact with the fatty material. When the blade is rotated, portions of the fatty material are shaved off and retained within the interior lumen of the catheter. This process is repeated until a sufficient amount of fatty material is removed and substantially normal blood flow is resumed.

In another procedure, stenosis within arteries and other blood vessels is treated by permanently or temporarily introducing a stent into the stenosed region to open the lumen of the vessel. The stent typically includes a substantially cylindrical tube or mesh sleeve made from such materials as stainless steel or nitinol. The design of the material permits the diameter of the stent to be radially expanded, while still providing sufficient rigidity such that the stent maintains its shape once it has been enlarged to a desired size.

Such percutaneous interventional procedures, i.e., angioplasty, atherectomy, and stenting, can dislodge material from the vessel walls. This dislodged material can enter the bloodstream. Some existing devices and technology use a filter for capturing the dislodged material from the bloodstream.

SUMMARY

This disclosure pertains to an embolic filter and method. Such a filter can include a guide wire, a filter element and a bridle connected to a filter support structure. Displacing the bridle with respect to the filter can partially elongates the support structure in a dimension generally parallel to the guide wire and narrows the support structure in a dimension generally perpendicular to the guide wire. This allows the elongated support structure to be drawn substantially within the lumen of a sheath for removal.

The inclusion of a linkage between a support structure at the proximal mouth of a filter element and the guide wire or guide tube about which a filter is deployed may, when combined with a retrieval bridle, assist in effecting a smooth transition between the fully deployed state of the filter and an at least partially collapsed state suitable for retrieval. The linkage may be formed, for example, by a wire wound about the guide wire (forming a coil) at one end, and formed as one piece with, or otherwise attached to the support structure at the other end. Attachment of the coil to the guide wire, if desired, may be accomplished by ordinary means such as an adhesive, soldering, crimping, and the like.

The filter element can be attached to a support structure which maintains the mouth of the filter in an open, deployed configuration and which may tend to seal the mouth of the filter across the lumen of vessel in which the filter is deployed. The support structure can be a nominally circular ring of wire or polymer which may be deformed by moderate radial forces. The support structure may be an elastomeric ring including a NiTi alloy such as nitinol.

A bridle can be attached to the support structure at a point which generally does not coincide with the point of attachment of the linkage to the support structure. The bridle may comprise one or more wires or strings which may be manipulated from the proximal end of the guide wire to deform the support structure. The bridle is generally configured to act in cooperation with the linkage to elongate the support structure in a dimension generally parallel to the guide wire and to narrow the support structure in a dimension generally perpendicular to the guide wire. Displacing the bridle proximally at least partially tilts the support structure relative to the guide wire. Desirable deformation of the support structure may be facilitated by the inclusion of a deadeye or block having a through hole fixed to the guide wire proximal to the deployed support structure such that pulling on the bridle which passes through the hole of the deadeye tends to narrow the support structure ring into an ellipse as the support structure deforms. In some embodiments, the function of the deadeye may be provided by the mouth of a catheter or sheath into which the support structure will be drawn.

BRIEF DESCRIPTION OF DRAWINGS

FIGS. 2A, 2C, and 2E are top views. FIGS. 2B, 2D, and 2F are side views.

FIGS. 4A, 4C, and 4E are top views. FIGS. 4B, 4D, and 4F are side views.

DETAILED DESCRIPTION

Figure 1:
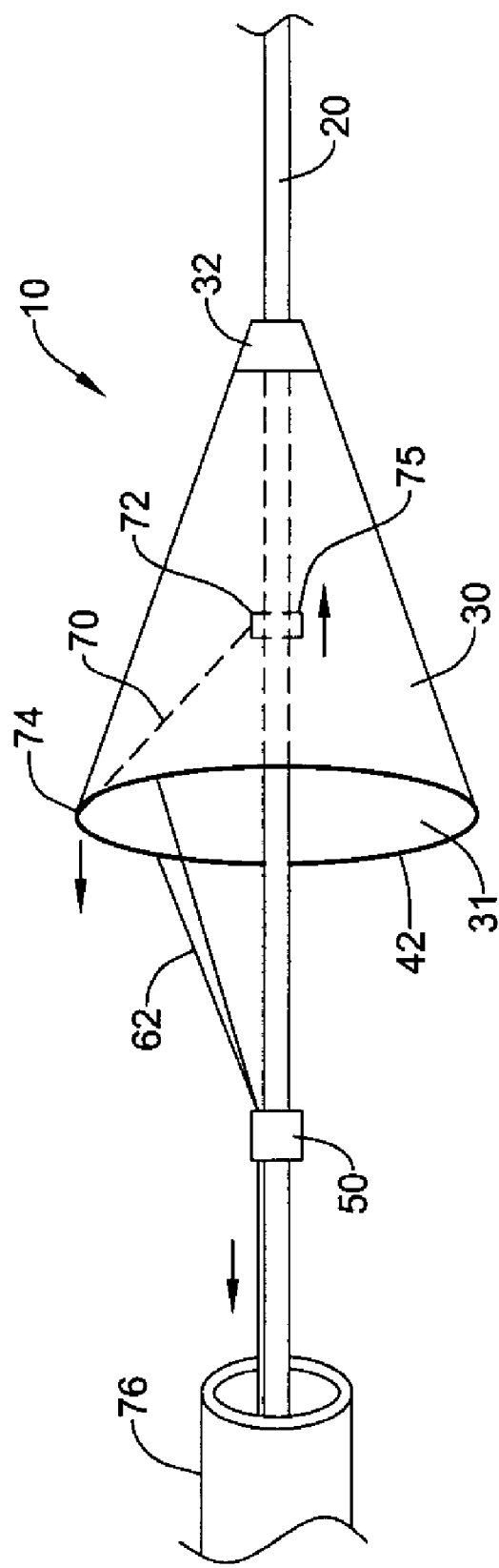
FIG. 1 illustrates a fully deployed embolic filter slightly rotated out of the plane to more clearly show attachment of a bridle to the support structure. Details of the filter have been omitted for clarity.

The following description should be read with reference to the drawings wherein like reference numerals indicate like elements throughout the several views. The drawings, which are not necessarily to scale, are not intended to limit the scope of the claimed invention. The detailed description and drawings illustrate example embodiments of the claimed invention.

All numbers are herein assumed to be modified by the term "about." The recitation of numerical ranges by endpoints includes all numbers subsumed within that range (e.g., 1 to 5 includes 1, 1.5, 2, 2.75, 3, 3.80, 4, and 5).

As used in this specification and the appended claims, the singular forms "a", "an", and "the" include the plural referents unless the content clearly dictates otherwise. As used in this specification and the appended claims, the term "or" is generally employed in its sense including "and/or" unless the content clearly dictates otherwise.

The embolic filters disclosed herein can include a guide wire, or tube, and advanced through a blood vessel until they are positioned downstream of an obstruction to be treated. The filters are then deployed in various ways, such as by withdrawing a catheter or sheath in which they had been compressed. These filters include several structural elements such as struts or rings which tend to bias a filter element consisting of a porous sheet or mesh in the form of a cone or basket toward expansion to completely span the lumen of the vessel to be protected. When the procedure has been completed, the filter is withdrawn by at least partially collapsing the filter and reintroducing the filter into a catheter or sheath to contain any captured emboli or other debris while the filter is withdrawn from the vessel.

FIG. 1, shows a filter 10 having a generally conical filter element 30 can be disposed about a guide wire or tube 20 having proximal and distal ends (not shown). A mouth 31 of the filter element 30 is generally circular and can be shaped by a support structure 42 in the form of a flexible ring which tends to expand the filter against a vessel wall. The ring may be formed from a NiTi alloy an biased to expand when exiting a delivery sheath (not shown). As illustrated, the detailed structure of the filter membrane has been omitted to allow the linkage 70 and its relationship with the guide wire 20 and the support structure 42 to be more clearly shown. It will be appreciated that the filter element 30 is generally formed from a sheet or mesh having holes large enough to allow blood cells to pass freely through the filter while emboli and other debris will remain trapped within the filter element. In this embodiment, the filter element 30 is supported proximally by support ring 42 and distally by a collar 32 which can be fixed to the guide wire 20 or linkage 70 is pivotably attached to the support structure 42 at a first point 74 and slideably attached to the guide wire 20 at a second point 72.

Bridle 62 which can include 2 wires, is also attached to the support structure 42 at points about its perimeter which can be generally symmetrically situated 90 degrees or less from the attachment point 74 of the linkage 70. The bridle 62 may slidably pass through a deadeye 50 attached to the guide wire 20. If the deadeye 50 is employed, it tends to cause the bridle 62 to narrow the support structure 42 as the bridle is withdrawn proximally. The bridle wires 62 may extend to the proximal end of wire 20.

Filter element 30 may be formed from a continuous sheet, a pre-perforated sheet, or a woven mesh. It may be formed of any material which is sufficiently flexible and compatible with bodily fluids such as blood. Examples of suitable materials include polyurethane, polyolefin, polyester, and silicone polymers. Assembly of the combined filter element as well as other structures which make up the filter may employ materials and methods such as adhesives, sewing, solvent welding, ultrasonic welding, crimping, and the like.

The entire sheet from which filter element 30 is formed may be perforated. The fabrication process punches or drills holes through at least the portion of the sheet which will form filter element 30 in order to provide fluid communication between the interior of the filter and the exterior of filter element 30.

Figure 2A:
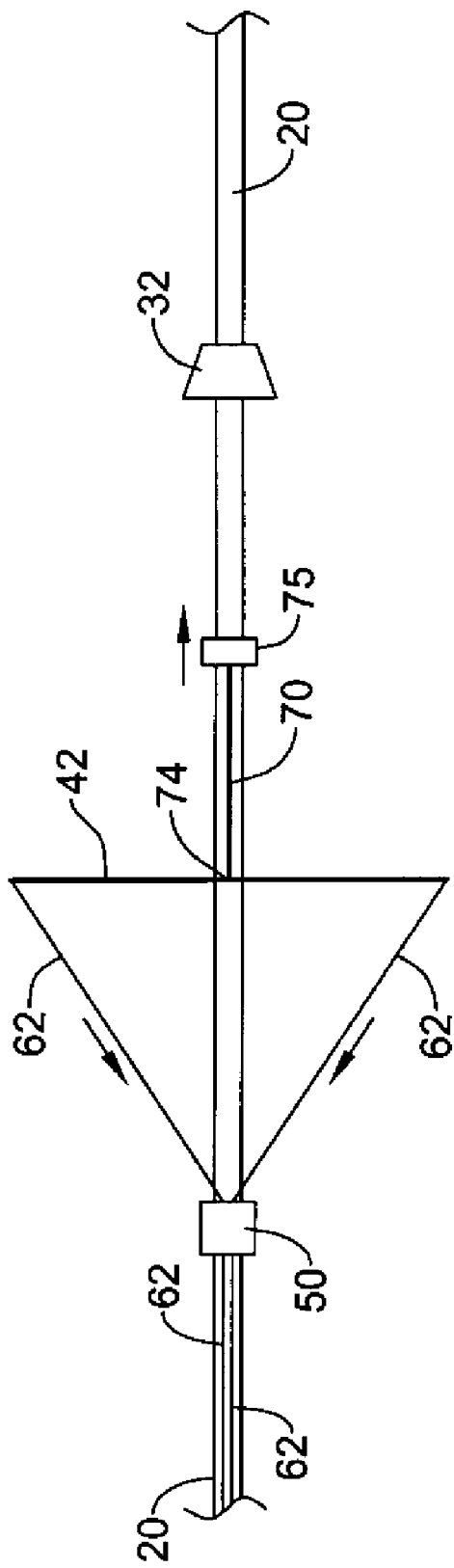
FIGS. 2A-2F are schematic representations of certain elements of the filter of FIG. 1 in various stages of collapse.
Figure 2B:
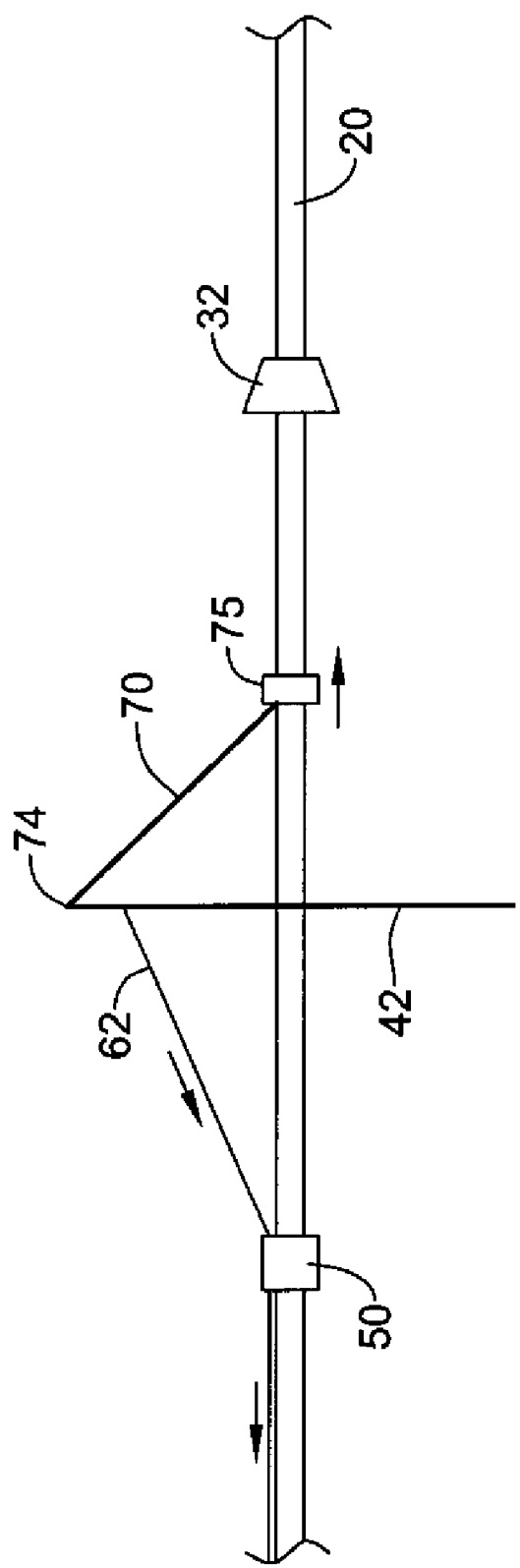
Figure 2C:
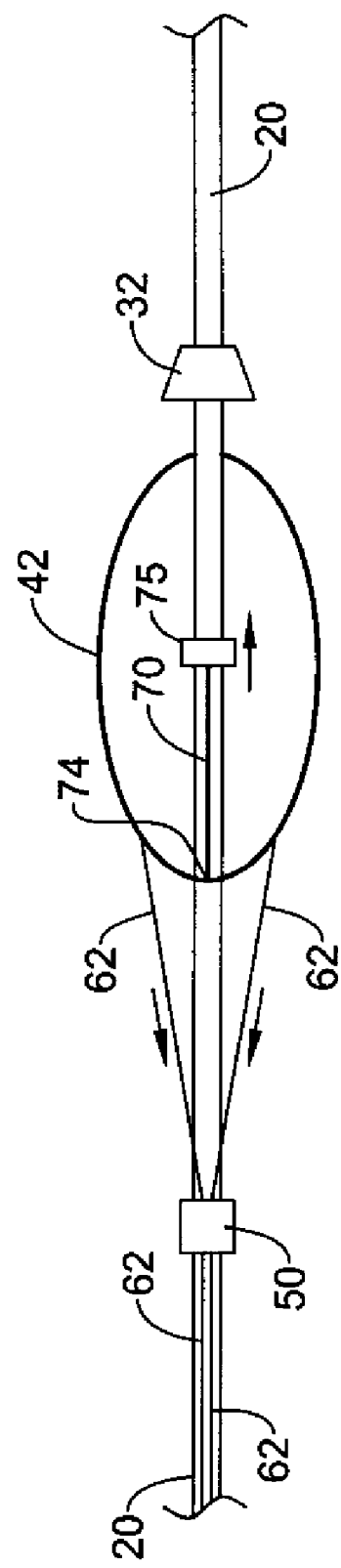
Figure 2D:
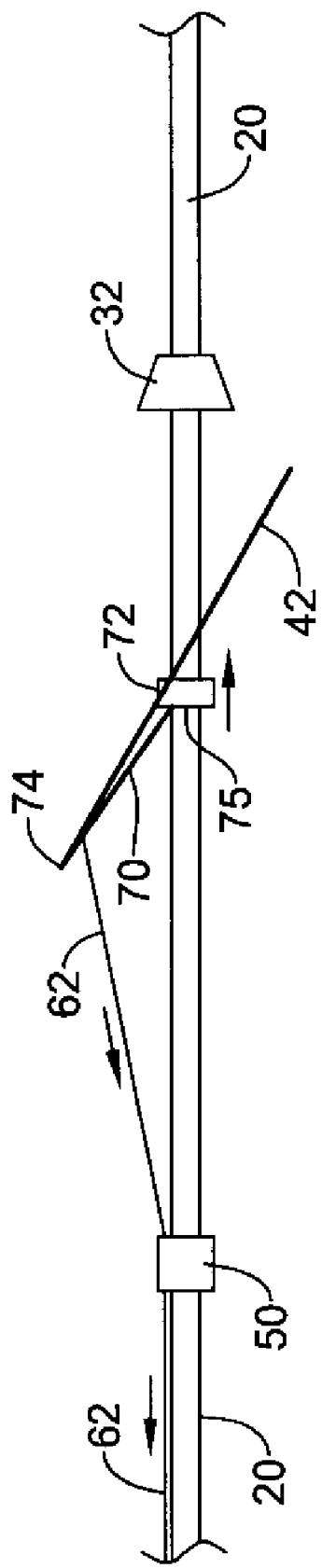
Figure 2E:
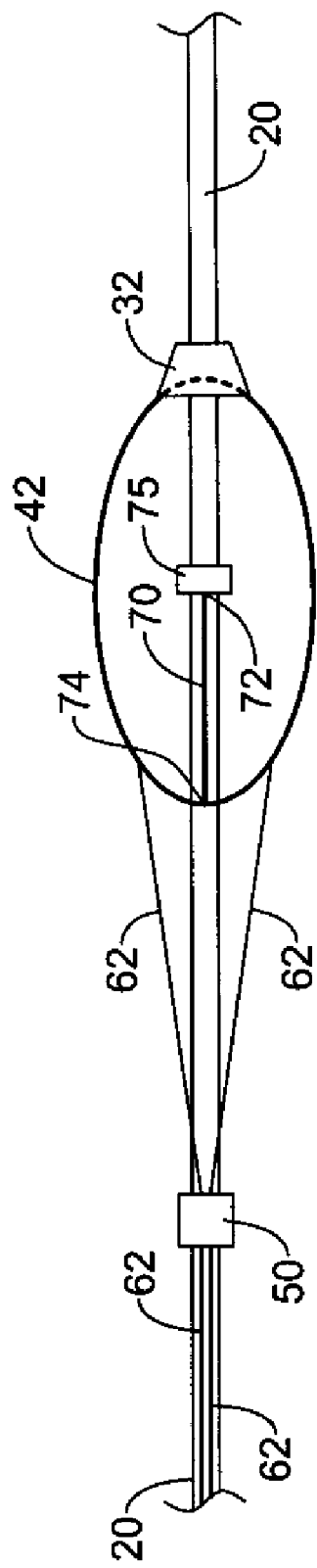
Figure 2F:
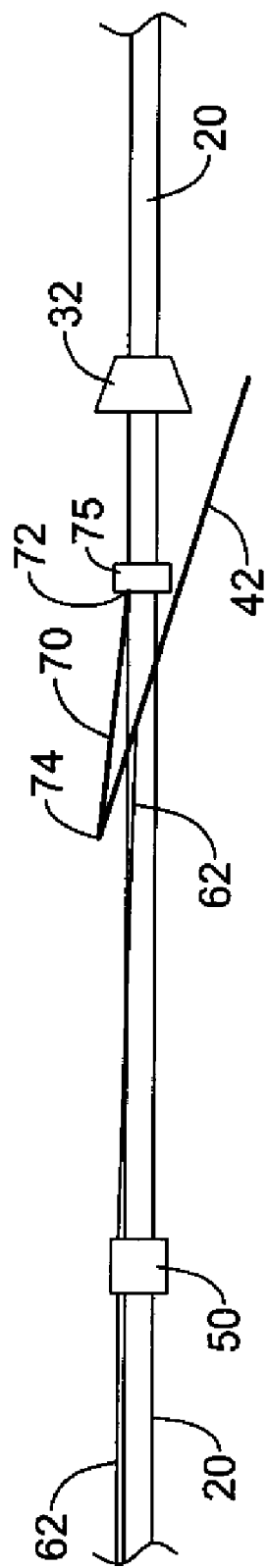

As shown in FIG. 1, collar 32 is fixed to guide wire 20 and the linkage 70 is slideably disposed about the guide wire. Since the relative displacement between the collar 32 and the most proximal part of the support structure 42 is limited by the elasticity of filter element 30, pulling bridle 62 proximally, tends to pull point 74, at which linkage 70 is attached to support structure 42, toward guide wire 20 as the second end 72 of the linkage 70 slides distally. Second end 72 can be connected to a bushing or tube 75 slidably disposed on guide wire 20. Paired FIGS. 2A-2B, 2C-2D, and 2E-2F provide schematic views of the stages of the collapse of the support ring 42 and the attendant changes in the relative positions of the linkage 70, guide wire 20, and collar 32. The filter element has been omitted for clarity. FIGS. 2A, 2C, and 2E are top views of the elements. FIGS. 2B, 2D, and 2F are side views of the elements. As the bridle is moved proximally, the support structure ring narrows and elongates while second end 72 moves distally, facilitating withdrawal of the filter into a lumen of a catheter or sheath 76.

Figure 3:
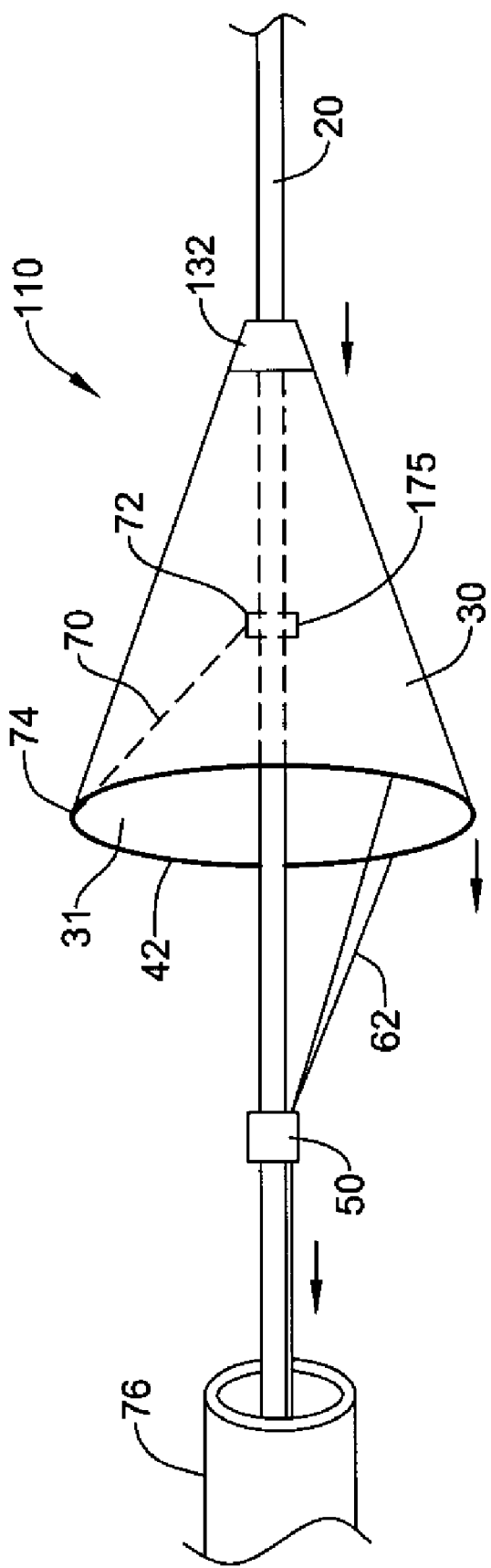
FIG. 3 illustrates a variant fully deployed embolic filter slightly rotated out of the plane to more clearly show attachment of a bridle to the support structure. Details of the filter have been omitted for clarity.

FIG. 3, shows a filter 110 which is similar to filter 110. In this embodiment, however, filter element 30 is supported proximally by the support structure 42 and distally by a collar 132 which is free to move along guide wire 20. Linkage 70 is pivotably attached to the support structure at first point 74 and fixed to the guide wire 20 at a second point 72 by a collar 175 or other device. Bridle 62 is also attached to the support structure 42 at points about its perimeter which can be generally symmetrically situated 90 degrees or more from the attachment point 74 of the linkage 70 but unlike filter 10, these points are opposite point 74.

Figure 4A:
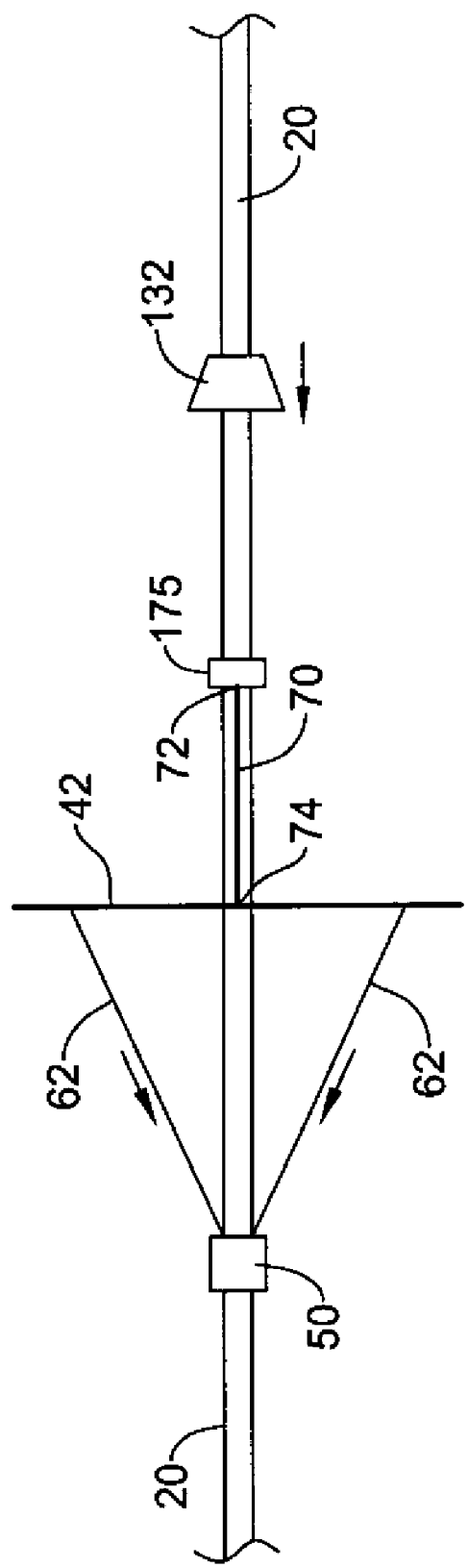
FIGS. 4A-4F are schematic representations of certain elements of the filter of FIG. 3 in various stages of collapse.
Figure 4B:
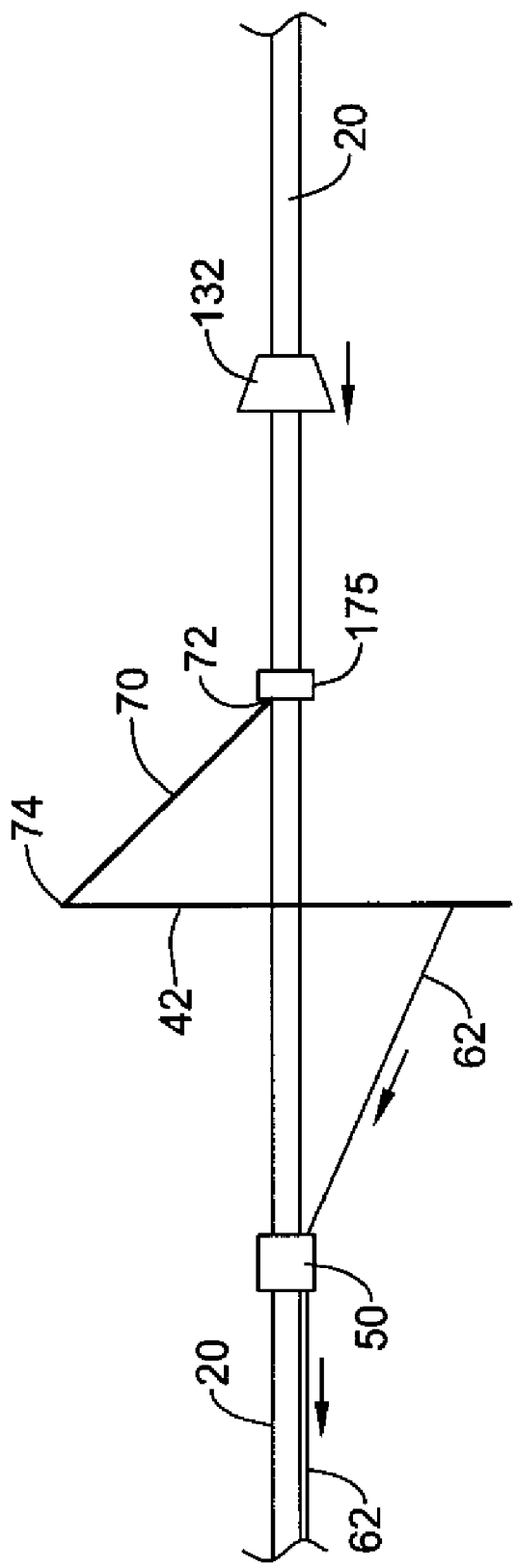
Figure 4C:
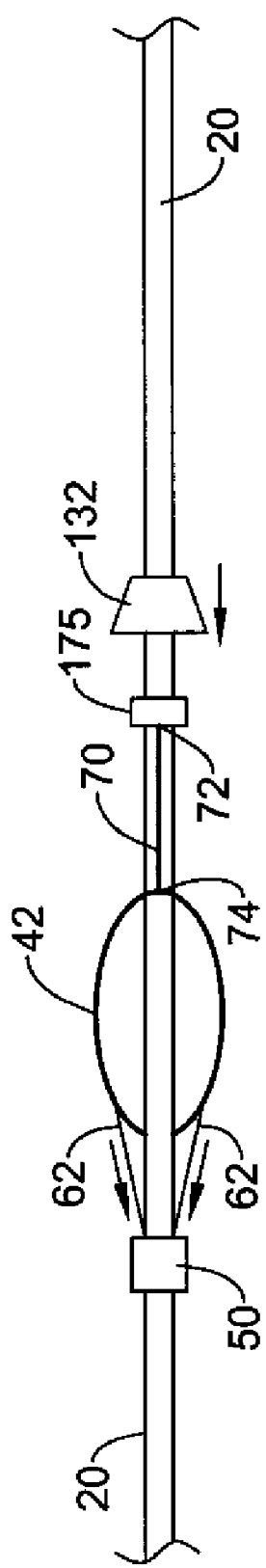
Figure 4D:
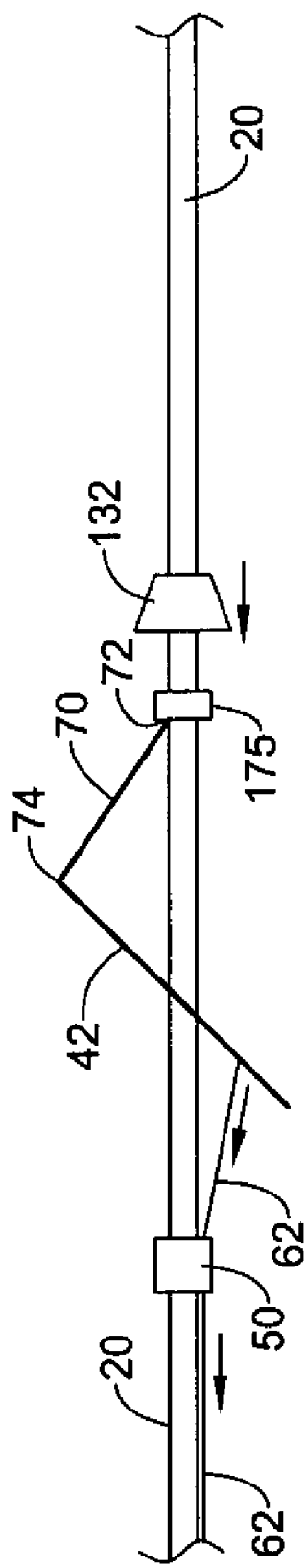
Figure 4E:
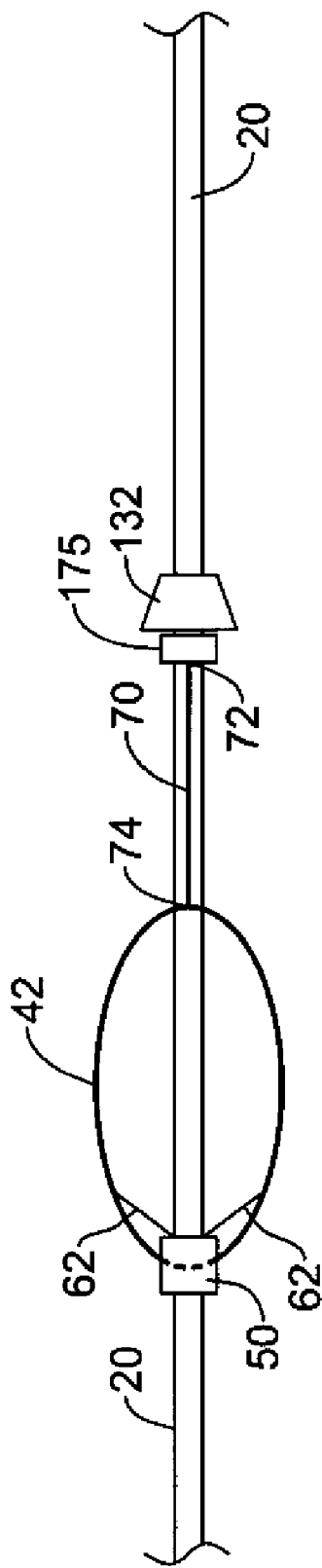
Figure 4F:
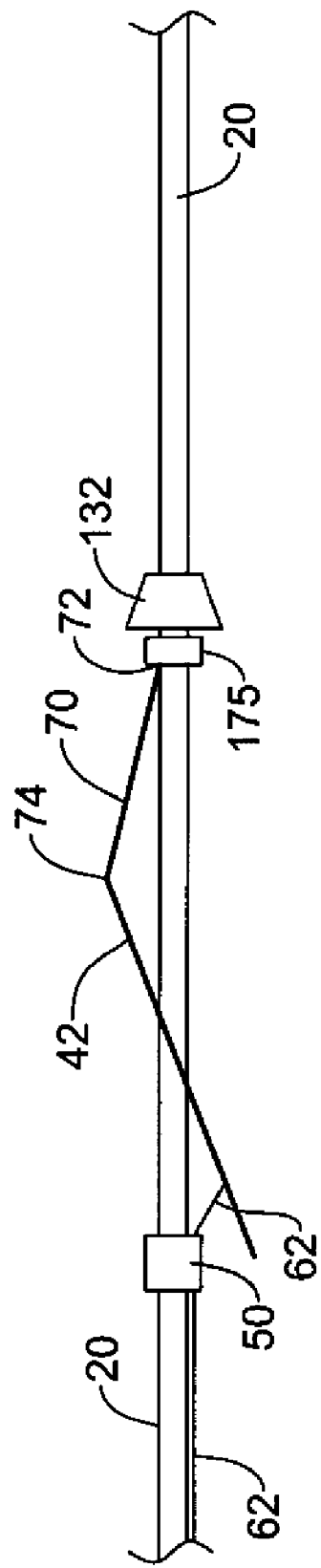

As shown in FIG. 3, collar 132 of filter 110 is free to move along guide wire 20 and linkage 70 is fixed to guide wire 20. Since the relative displacement between the collar 32 and the most proximal part of support structure 42 is limited by the elasticity of the filter element 30 (not shown in FIGS. 2A-E), pulling the bridle 62 proximally, tends to pull first point 74, at which linkage 70 is attached, to the support structure 42, toward the guide wire 20 as the second end 72 of the linkage 70 pivots about the fixed point of attachment to the guide wire. Paired FIGS. 4A-4B, 4C-4D, and 4E-4F provide schematic views of the stages of the collapse of the support ring 42 and the attendant changes in the relative positions of the linkage 70, guide wire 20, and collar 32. The filter element has been omitted for clarity. FIGS. 4A, 4C, and 4E are top views of the elements. FIGS. 4B, 4D, and 4F are side views of the elements. As bridle 62 is withdrawn, the support structure ring narrows and elongates facilitating withdrawal of the filter into a lumen of a catheter or sheath 76.

A number of option configurations of the filter can be made. For example, the bridle can include two or more wires or strings. A bridle comprising two or more strings may optionally extend the length of the guide wire without joining the wires or strings into a single unit or the two or more wires or strings may be consolidated proximal the support structure. Placement of the point(s) of attachment of the bridle to the support structure may advantageously be varied depending on the desired manner of retrieving the filter. If the linkage is attached to the top of the support structure and is fixed to the guide wire, attaching the bridle wire or string near the bottom of the support structure will facilitate tilting and elongation of the support structure such that the bottom of the support ring enters the a retrieval catheter or sheath before the top does. The distal end of the filter element will slide along the guidewire as the support structure collapses. Additionally, attaching two bridle wires to the support structure slightly below the widest part of the support structure and passing them through a deadeye located relatively close to the open mouth of the deployed support structure will tend to partially elongate the support structure in a dimension generally parallel to the guide wire and narrow the support structure in a dimension generally perpendicular to the guide wire bottom as the support structure distorts into a more elliptical configuration as the bridle is pulled proximately.

Although the illustrative examples described above relate to an embodiment in which the open mouth of the filter is directed proximally with respect to the guide wire, a reversal of the filter components is also contemplated. In such an embodiment, the deadeye would be mounted distally with respect to the mouth of the filter element and the bridle would be folded back at the deadeye to lie generally along the guide wire as it passes the filter element.

Various modifications and alterations of this invention will become apparent to those skilled in the art without departing from the scope and principles of this invention, and it should be understood that this invention is not to be unduly limited to the illustrative embodiments set forth hereinabove. All publications and patents are herein incorporated by reference to the same extent as if each individual publication or patent was specifically and individually indicated to be incorporated by reference.

What is claimed is:

1. An embolic filter comprising:
   a guide wire;
   a filter element having a proximal opening disposed about the guide wire;
   a support structure connected to the proximal opening of the filter element;
   a linkage having attachment points on the support structure and the guide wire; and
   a bridle connected to the support structure remotely from the attachment point between the linkage and the support structure;
   wherein the bridle includes a first wire attached to the support structure at a first point remote from the attachment point between the linkage and the support structure, and a second wire attached to the support structure at a second point remote from the attachment point between the linkage and the support structure;
   wherein the first point and the second point are positioned on the support structure generally symmetrically about the attachment point between the linkage and the support structure;
   wherein the linkage extends distally from the attachment point on the support structure;
   wherein the bridle extends from the support structure to a proximal end of the guide wire; wherein displacing the bridle proximally at least partially tilts the support structure about the guide wire.

2. The embolic filter of claim 1, wherein the support structure is a flexible ring.

3. The embolic filter of claim 1, wherein the linkage having attachment points on the support structure and the guide wire; wherein the linkage is slideably attached to the guide wire.

4. The embolic filter of claim 3, wherein the distal end of the filter element is fixedly attached to the guide wire.

5. The embolic filter of claim 1, wherein the linkage having attachment points on the support structure and the guide wire; wherein the linkage is fixedly attached to the guide wire.

6. The embolic filter of claim 5, wherein the distal end of the filter element is slideably attached to the guide wire.

7. The embolic filter of claim 1, wherein the filter element comprises a sheet or mesh having a plurality of openings therethrough providing fluid communication between at least a portion of its two major surfaces.

8. The embolic filter of claim 1, further comprising a deadeye, fixed to the guide wire proximal the support structure, having an opening through which the bridle passes.

9. The embolic filter of claim 1, wherein displacing the bridle proximally at least partially elongates the support structure in a dimension generally parallel to the guide wire and narrows the support structure in a dimension generally perpendicular to the guide wire.

10. A method of retrieving an embolic filter comprising:
    providing a guide wire;
    providing a filter element having a proximal opening disposed about the guide wire;
    providing a support structure connected to the proximal opening of the filter element;
    providing a linkage having attachment points on the support structure and the guide wire;
    providing a bridle connected to the support structure remotely from the attachment point between the linkage and the support structure;
    wherein the bridle includes a first wire attached to the support structure at a first point remote from the attachment point between the linkage and the support structure, and a second wire attached to the support structure at a second point remote from the attachment point between the linkage and the support structure;
    wherein the first point and the second point are positioned on the support structure generally symmetrically about the attachment point between the linkage and the support structure;
    wherein the linkage extends distally from the attachment point on the support structure;
    wherein the bridle extends from the support structure to a proximal end of the guide wire; and
    withdrawing the bridle proximally to at least partially elongate the support structure in a dimension generally parallel to the guide wire and to narrow the support structure in a dimension generally perpendicular to the guide wire; wherein displacing the bridle proximally at least partially tilts the support structure about the guide wire.

11. The method of claim 10 further comprising providing a sheath associated with, and slideable relative to, the guide wire, wherein the sheath has a lumen adapted to contain the at least partially elongated support structure and further withdrawing the bridle until the support structure is substantially within the lumen of the sheath.

* * * * *